United States Patent [19]

Singleton

[11] Patent Number: 5,320,836
[45] Date of Patent: Jun. 14, 1994

[54] HAIR SPRAY FORMULATIONS CONTAINING A POLYETHYLENE GLYCOL ESTER OF CAPRYLIC AND CAPRIC ACIDS

[75] Inventor: Andy H. Singleton, Kingsport, Tenn.

[73] Assignee: Eastman Kodak Company, Rochester, N.Y.

[21] Appl. No.: 353

[22] Filed: Jan. 4, 1993

[51] Int. Cl.$^5$ ............................................. A61K 7/11
[52] U.S. Cl. .............................. 424/71; 424/DIG. 1; 424/DIG. 2; 424/47; 424/78.02
[58] Field of Search ............ 424/47, DIG. 1, DIG. 2, 424/70, 71, 45, 78.02

[56] References Cited

U.S. PATENT DOCUMENTS 4,300,580  11/1981  O'Neill et al. ..................... 132/7
5,030,443   7/1991  Varco et al. ...................... 424/47
5,158,762  10/1992  Pierce .............................. 424/71

OTHER PUBLICATIONS

Eastman Kodak Co. (1989). Eastman AQ® Polymers: Properties and Applications, Publication No. GN–389.

*Primary Examiner*—Thurman K. Page
*Assistant Examiner*—Raj Bawa
*Attorney, Agent, or Firm*—John D. Thallemer

[57] ABSTRACT

This invention relates to hair spray formulations which eliminate flaking. The hair spray formulations are based on (1) a sulfonate-containing, water-dispersible or water-dissipatible, linear polyester having a glass transition temperature of 33° C. to 60° C., (2) a polyethylene glycol ester of a mixture of caprylic and capric acids, (3) an alpha-hydroxy carboxylic acid having 2 to 6 carbon atoms, and (4) water or a water/alcohol mixture.

19 Claims, No Drawings

HAIR SPRAY FORMULATIONS CONTAINING A POLYETHYLENE GLYCOL ESTER OF CAPRYLIC AND CAPRIC ACIDS

FIELD OF THE INVENTION

This invention relates to hair spray formulations which eliminate flaking. The hair spray formulations are based on (1) a sulfonate containing, water dispersible or water dissipatible, linear polyester having a glass transition temperature of 33° C. to 60° C., (2) a polyethylene glycol ester of a mixture of caprylic and capric acids, (3) an alpha hydroxy carboxylic acid having 2 to 6 carbon atoms, and (4) water or a water/alcohol mixture.

BACKGROUND OF THE INVENTION

Hair spray formulations typically comprise a solution of a polymer, the fixative, in water/alcohol mixtures. The polymeric materials which are typically used in hair spray formulations are soluble in water or water/alcohol mixtures and are derived from N-vinylpyrrolidinone or N-vinylpyrrolidinone and one or more other vinyl monomers such as vinyl acetate, acrylate and methacrylate esters and/or styrene compounds. When applied to hair and allowed to dry, the polymeric material provides human hair body, consistency, and firm texture, however, such materials have the disadvantage of flaking.

U.S. Pat. No. 4,300,580 describes hair spray formulations containing a water-dispersible or water-dissipatible linear sulfo-polyester fixative in a water/alcohol mixture. Such formulations are fast drying and have good hair holding properties but possess the disadvantage of being very difficult to remove from the hair. For example, prolonged washing is required to completely remove the water dispersible, linear polyester fixative to obtain hair with no tacky or sticky feel. In an effort to overcome the fixative removal problem, U.S. Pat. No. 4,300,580 teaches the addition of certain water soluble polymers to formulations containing the water-dispersible, linear polyester. The use of poly(alkylene glycols) such as poly(ethylene glycol) is disclosed. However, when such formulations containing a combination of the poly(alkylene glycol) and water-dispersible, linear polyester are applied to hair and allowed to dry, the fixative causes a matting of the hair. Such matting hinders combing, brushing and styling of hair.

U.S. Pat. No 5,030,443 discloses alginate hair setting compositions which contain an antiflaking polymer agent having one or more carboxylic acid groups. The carboxylated polymers are polyacrylic and polymethacrylic acids which are used in their acid form to facilitate crosslinking.

In contrast, the present inventor has unexpectedly discovered hair spray formulations that provide human hair with body, consistency, and firm texture, without the disadvantages described hereinabove, such as flaking, tackiness, matting and difficulty in removal. The formulations of this invention may be sprayed on dry or damp hair by means of an aerosol or pump to provide a thin transparent film enhancing the natural luster of the hair without imparting a lacquered appearance thereto. The deposited film has sufficient strength to keep the hair in place, even under conditions of high humidity, but without stiffening the hair. The hair spray dries quickly to a non tacky state which does not flake on combing but is easily removed by washing with water and mild soap or commercial shampoo preparations.

SUMMARY OF THE INVENTION

Accordingly, it is one object of the present invention to provide a hair spray formulation which eliminates flaking.

Accordingly, it is another object of the invention to provide an aerosol hair spray formulation which is not tacky, has a fast drying rate, acceptable body, consistency and firm texture necessary to hold hair in the desired arrangement for a certain length of time.

Still another object of the invention is to provide a hair spray formulation having excellent storage stability and which does not clog or produce foam at the exit port of an aerosol or pump container.

These and other objects are accomplished herein by a hair spray composition comprising:

(1) a sulfo-polyester having a Tg of 33° C. to 60° C. consisting essentially of repeat units from
  (a) a dicarboxylic acid selected from the group consisting of aromatic dicarboxylic acids, saturated aliphatic dicarboxylic acids, cycloaliphatic dicarboxylic acids, and combinations thereof;
  (b) a diol; and
  (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol;

(2) a polyethylene glycol ester of a mixture of caprylic and capric acids which is selected from the group consisting of

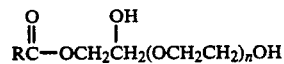

and mixtures thereof,
wherein R is $CH_3(CH_2)_n$ and n is 4 to 10;

(3) an alpha hydroxy carboxylic acid having 2 to 6 carbon atoms; and (4) a liquid vehicle selected from the group consisting of water and a water/alcohol mixture.

DESCRIPTION OF THE INVENTION

The term "hair" as used in the present invention includes treated and untreated human hair, animal hair, and any type of fiber which requires consistency and firm texture necessary to hold it in the desired arrangement for a certain length of time.

The sulfo polyester, component (1), has a glass transition temperature in the critical range of about 33° C. to about 60° C. and contains repeat units from a dicarboxylic acid, a diol and a difunctional sulfomonomer. Dicarboxylic acids useful in the present invention include aromatic dicarboxylic acids preferably having 8 to 14 carbon atoms, saturated aliphatic dicarboxylic acids preferably having 4 to 12 carbon atoms, and cycloaliphatic dicarboxylic acids preferably having 8 to 12 carbon atoms. Specific examples of dicarboxylic acids are: terephthalic acid, phthalic acid, isophthalic acid, naphthalene-2,6-dicarboxylic acid, cyclohexanedicarboxylic acid, cyclohexanediacetic acid, diphenyl 4,4'-dicarboxylic acid, succinic acid, glutaric acid, adipic acid, azelaic acid, sebacic acid, and the like. The polyester may be prepared from two or more of the above dicarboxylic acids.

It should be understood that use of the corresponding acid anhydrides, esters, and acid chlorides of these acids is included in the term "dicarboxylic acid".

The diol component of the polyester includes cycloaliphatic diols preferably having 6 to 20 carbon atoms or aliphatic diols preferably having 3 to 20 carbon atoms. Examples of such diols are: ethylene glycol, diethylene glycol, triethylene glycol, 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropane-diol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethyl-cyclobutane, 2,2-bis-(3-hydroxyethoxyphenyl)-propane, and 2,2-bis-(4-hydroxypropoxyphenyl)-propane. The polyester may be prepared from two or more of the above diols.

The difunctional sulfomonomer component of the polyester may be a dicarboxylic acid or an ester thereof containing a sulfonate group ($-SO_3^-$), a diol containing a sulfonate group, or a hydroxy acid containing a sulfonate group. The cation of the sulfonate salt may be $Na+$, $Li+$, $K+$, $NH_4+$, and substituted ammonium. The term "substituted ammonium" refers to ammonium substituted with an alkyl or hydroxy alkyl radical having 1 to 4 carbon atoms. The difunctional sulfomonomer contains at least one sulfonate group attached to an aromatic nucleus wherein the functional groups are hydroxy, carboxy or amino. Advantageous difunctional sulfomonomer components are those wherein the sulfonate salt group is attached to an aromatic acid nucleus such as benzene, naphthalene, diphenyl, oxydiphenyl, sulfonyldiphenyl or methylenediphenyl nucleus. Preferred results are obtained through the use of sulfophthalic acid, sulfoterephthalic acid, sulfoisophthalic acid, 4-sulfonaphthalene-2,7-dicarboxylic acid, and their esters. The sulfomonomer is present in an amount from 4 to 25 mole percent, preferably 10 to 12 mole percent, based on 100 mole percent dicarboxylic acid and 100 mole percent diol.

In particularly preferred embodiments, the water dispersible sulfo-containing linear polyester is derived from a mixture of dicarboxylic acids consisting of isophthalic acid (or ester) and 5-sodio-sulfoisophthalic acid, a diol component consisting of diethylene glycol, or a mixture of diols consisting of at least 75 mole percent of diethylene glycol with the remaining diol being either ethylene glycol or 1,4-cyclohexane-dimethanol. The sulfo polyester, component (1), is present in an amount of about 1 to about 10 weight percent, based on the weights of components (1), (2), (3) and (4) of the hair spray formulation.

Component (2) of the hair spray is a polyethylene glycol ester of a mixture of caprylic and capric acids which is selected from the group consisting of

and mixtures thereof wherein R is $CH_3(CH_2)_n$ and n is 4 to 10. Suitable examples include polyethylene glycol 400 monocaprate, polyethylene glycol 400 monocaprylate, polyethylene glycol 400 caprylate/caprate and polyethylene glycol 300 caprylic/capric glycerides. A preferred polyethylene glycol ester of a mixture of caprylic and capric acids is

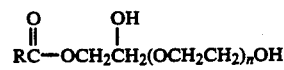

wherein RCO is a mixture of caprylic and capric radicals and n has an average value of 6.

Component (3) of the hair spray is an alpha-hydroxy carboxylic acid which has 2 to 6 carbon atoms. A preferred alpha-hydroxy carboxylic acid is lactic acid. The alpha-hydroxy carboxylic acid may be added in neat form or in solution with water, such as a 50/50 acid/water weight percent solution.

Component (4) of the hair spray is a liquid vehicle. The liquid vehicle of the formulations may be water or a water/alcohol mixture. Distilled or deionized water are the preferred sources of water since tap water generally contains ions which would precipitate the sulfopolyester, component (1). The alcohol should have two to four carbon atoms. Specific alcohols include, ethanol, isopropanol and t-butanol.

The present inventor has determined that for aerosol hair sprays, the liquid vehicle is preferably water. However, a water/alcohol mixture may be employed as long as the alcohol is present in an amount less than about 50 weight percent. In such aerosol hair spray formulations where an alcohol/water mixture is employed, preferably 35 to 45 weight percent of the mixture is alcohol. In pump formulations, the liquid vehicle may consist of up to 80 weight percent alcohol. The preferred alcohol is ethanol. The liquid vehicle is present in an amount of about 46 to about 94 weight percent, based on the weights of components (1), (2), (3) and (4) of the hair spray formulation. Preferably, the liquid vehicle is present in an amount of 55 to 70 weight percent, based on the weights of components (1), (2), (3) and (4) of the hair spray formulation.

For aerosol hair spray formulations, a propellant selected from the group consisting of a $C_1$-$C_4$ aliphatic hydrocarbons and dimethyl ether, is necessary. The aliphatic hydrocarbons may be branched or straight chain and include methane, ethane, propane, n-butane, isobutane, or mixtures thereof. A preferred aliphatic hydrocarbon propellant is a mixture containing about 83 percent isobutane and about 17 percent propane. The propellant is present in an amount of about 3 to about 40 weight percent, based on the weights of components (1), (2), (3) and (4) of the aerosol hair spray formulation. In the case where a $C_1$-$C_4$ aliphatic hydrocarbon is used as the propellant, generally about 3 to about 10 weight percent, preferably 4 to 7 weight percent, is employed. In the case where dimethyl ether is used as the propellant, generally, about 30 to about 40 weight percent, preferably, 30 to 35 weight percent, is employed.

Other conventional additives such as preservatives, fragrances, antifoaming agents, hair conditioners, plasticizers, etc. may be added in such quantities as desired, up to about 5.0% by weight of the total formulation. Although the film forming formulations described herein are particularly useful as aerosol hair sprays for the grooming of hair, it is possible that the formulations, with or without modification, may be used in other types of personal care products.

The materials and testing procedures used for the results shown herein are as follows:

DYMEL A (CTFA Adopted Name: Dimethyl Ether) available from DuPont, is a dimethyl ether.

FINSOLV PL-355 is available from Finetex, is an alkoxylated alcohol ester.

Dow Corning 190 Surfactant (CTFA Adopted Name: Dimethicone Copolyol) available from Dow Corning, is a polymer of dimethylsiloxane with polyoxyethylene and/or polyoxypropylene side chains.

SOFTIGEN 767 is available from Hüls, is a polyethylene glycol caprylic/capric monoglyceride.

Inherent viscosity (I.V.) was measured at 23° C. using 0.50 grams of polymer per 100 ml of a solvent consisting of 60% by weight phenol and 40% by weight tetrachloroethane.

Preparation of tresses involved natural brown, European virgin hair. About two grams of hair, root end, were glued to a 2" by 2" plastic tab. The tresses were cut so that the length of hair hanging below the tabs was six inches.

Preparation of the 28% dispersions of water-dispersible sulfo-polyester:

A. Sulfo-Polyester A was prepared as follows: A 500 mL round bottom flask equipped with a ground-glass head, an agitator shaft, nitrogen inlet and a side arm was charged with 74.0 grams of isophthalic acid, 16.0 grams of 5-sodiosulfoisophthalic acid, 106.0 grams of diethylene glycol, sufficient titanium isopropoxide to provide 50 ppm of titanium, and 0.45 grams of sodium acetate tetrahydrate. The flask was immersed in a Belmont bath at 200° C. for two hours under a nitrogen sweep. The temperature of the bath was increased to 280° C. and the flask was heated for one hour under reduced pressure of 0.5 to 0.1 mm of Hg. The flask was allowed to cool to room temperature and the copolyester was removed from the flask. The copolyester had an I.V. of about 0.45 and a glass transition temperature of about 30° C. as measured using a differential scanning calorimeter (DSC). The copolyester was extruded and pelletized.

A 28% solids dispersion of Sulfo-Polyester A in water was prepared by heating the water to a temperature of 75° C. to 85° C. and adding the required amount of pellets while agitating at a rate sufficient to maintain the pellets in suspension. The heating was continued until all the pellets were dispersed, approximately, 20 to 30 minutes. Water was added to replace evaporation loss. The dispersion was cooled and filtered.

B. Sulfo-Polyester B was prepared as follows: A 500 mL round bottom flask equipped with a ground-glass head, an agitator shaft, nitrogen inlet and a side arm was charged with 74.0 grams of isophthalic acid, 16.0 grams of 5-sodiosulfoisophthalic acid, 83.0 grams of diethylene glycol, 16.0 grams of 1,4-cyclohexane-dimethanol, sufficient titanium isopropoxide to provide 50 ppm of titanium, and 0.45 grams of sodium acetate tetrahydrate. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 10 mm of Hg. The flask was allowed to cool to room temperature and the copolyester was removed from the flask. The copolyester had an I.V. of about 0.36 and a glass transition temperature of about 38° C. as measured using a differential scanning calorimeter (DSC). The copolyester was extruded and pelletized.

A 28% solids dispersion of Sulfo-Polyester B in water was prepared by heating the water to a temperature of 90° C. to 95° C. and adding the required amount of pellets while agitating at a rate sufficient to maintain the pellets in suspension. The heating was continued until all the pellets were dispersed, approximately, 20 to 30 minutes. Water was added to replace evaporation loss. The dispersion was cooled and filtered.

C. Sulfo-Polyester C was prepared as follows: A 500 mL round bottom flask equipped with a ground-glass head, an agitator shaft, nitrogen inlet and a side arm was charged with 136.0 grams of isophthalic acid, 53.0 grams of 5-sodiosulfoisophthalic acid, 155.0 grams of diethylene glycol, 78.0 grams of 1,4-cyclohexane-dimethanol, sufficient titanium isopropoxide to provide 50 ppm of titanium, and 1.48 grams of sodium acetate tetrahydrate. The flask was immersed in a Belmont bath at 200° C. for one hour under a nitrogen sweep. The temperature of the bath was increased to 230° C. for one hour. The temperature of the bath was increased to 280° C. and the flask was heated for 45 minutes under reduced pressure of 0.5 to 0.1 mm of Hg. The flask was allowed to cool to room temperature and the copolyester was removed from the flask. The copolyester had an I.V. of about 0.33 and a glass transition temperature of about 55° C. as measured using a differential scanning calorimeter (DSC). The copolyester was extruded and pelletized.

A 28% solids dispersion of Sulfo-Polyester C in water was prepared by heating the water to a temperature of 85° C. to 90° C. and adding the required amount of pellets while agitating at a rate sufficient to maintain the pellets in suspension. The heating was continued until all the pellets were dispersed, approximately, 20 to 30 minutes. Water was added to replace evaporation loss. The dispersion was cooled and filtered.

The invention will be further illustrated by a consideration of the following examples, which are intended to be exemplary of the invention. All parts and percentages in the examples are on a weight basis unless otherwise stated.

EXAMPLE I

Hair spray was prepared according to the following formulation:

| Ingredient | Weight % |
| --- | --- |
| Distilled Water | 57.97 |
| HYDROTRITICUM WAA | 0.20 |
| 28% Dispersion of Sulfo-Polyester A | 40.83 |
| SOFTIGEN 767 | 1.00 |

This hair spray formulation was prepared by adding the HYDROTRITICUM WAA, the 28% dispersion of Sulfo-Polyester A, and SOFTIGEN 767 to the water and mixing until well dispersed. The pH was determined to be 5.0 to 5.5. A 70/30 ratio of the hair spray to dimethyl ether was prepared. The formulation was applied in the form of an aerosol hair spray to hair tresses. The hair treated with the aerosol hair spray had a tacky or sticky feel.

EXAMPLE II

Hair spray was prepared according to the following formulation:

| Ingredient | Weight % |
| --- | --- |
| Distilled Water | 57.97 |
| HYDROTRITICUM WAA | 0.20 |
| 28% Dispersion of Sulfo-Polyester B | 40.83 |
| SOFTIGEN 767 | 1.00 |

This hair spray formulation was prepared by adding the HYDROTRITICUM WAA, the 28% dispersion of Sulfo-Polyester A, and SOFTIGEN 767 to the water and mixing until well dispersed. The pH was determined to be 5.0 to 5.5. A 70/30 ratio of the hair spray to dimethyl ether was prepared. The aqueous aerosol formulation showed good clarity and storage stability for a period of at least 3 months. The formulation was applied in the form of an aerosol hair spray to hair tresses. A minor amount of flaking was observed after drying and brushing the tresses.

EXAMPLE III

Hair spray was prepared according to the following formulation:

| Ingredient | Weight % |
| --- | --- |
| Distilled Water | 56.47 |
| HYDROTRITICUM WAA | 0.20 |
| 28% Dispersion of Sulfo-Polyester B | 40.83 |
| 50% Solution of Lactic Acid | 2.00 |
| 50% Solution of Sodium Hydroxide | 0.50 |

This hair spray formulation was prepared by adding sodium hydroxide to the lactic acid such that the pH was 4.0 to 5.5. The solution was then combined with water. HYDROTRITICUM WAA and the 28% dispersion of Sulfo-Polyester B were added to the water solution and mixed until well dispersed. A 70/30 ratio of the hair spray to dimethyl ether was prepared. The formulation was applied in the form of an aerosol hair spray to hair tresses. Flaking was observed after drying and brushing the tresses.

EXAMPLE IV

Hair spray was prepared according to the following formulation:

| Ingredient | Weight % |
| --- | --- |
| Distilled Water | 55.47 |
| 50% Solution of Lactic Acid | 2.00 |
| 50% Solution of Sodium Hydroxide | 0.50 |
| HYDROTRITICUM WAA | 0.20 |
| 28% Dispersion of Sulfo-Polyester B | 40.83 |
| SOFTIGEN 767 | 1.00 |

This hair spray formulation was prepared by adding sodium hydroxide to the lactic acid such that the pH was 4.0 to 5.5. The solution was then combined with water. HYDROTRITICUM WAA, the 28% dispersion of Sulfo-Polyester B, and SOFTIGEN 767 were added to the water solution and mixed until well dispersed. The hair spray formulation was applied to hair tresses by means of a pump. No flaking was observed after drying and brushing the tresses. In addition, the hair spray formulation provided the hair with good hold properties without a tacky or sticky feel.

EXAMPLE V

A 70/30 ratio of the hair spray prepared in Example III to dimethyl ether was prepared. The aqueous aerosol formulation showed good clarity and storage stability for a period of at least 3 months. The formulation was applied in the form of an aerosol hair spray to hair tresses. No flaking was observed after drying and brushing the tresses. In addition, the hair spray formulation provided the hair with good hold properties without a tacky or sticky feel.

EXAMPLE VI

A 70/30 ratio of the hair spray prepared in Example III to a mixture containing about 83 percent isobutane and about 17 percent propane was prepared. The aqueous aerosol formulation showed good clarity and storage stability for a period of at least 3 months. The formulation was applied in the form of an aerosol hair spray to hair tresses. No flaking was observed after drying and brushing the tresses. In addition, the hair spray formulation provided the hair with good hold properties without a tacky or sticky feel.

EXAMPLE VII

Hair spray was prepared according to the following formulation:

| Ingredient | Weight % |
| --- | --- |
| Distilled Water | 55.47 |
| 50% Solution of Lactic Acid | 2.00 |
| 50% Solution of Sodium Hydroxide | 0.50 |
| HYDROTRITICUM WAA | 0.20 |
| 28% Dispersion of Sulfo-Polyester C | 40.83 |
| SOFTIGEN 767 | 1.00 |

This hair spray formulation was prepared by adding sodium hydroxide to the lactic acid such that the pH was 4.0 to 5.5. The solution was then combined with water. HYDROTRITICUM WAA, the 28% dispersion of Sulfo-Polyester C, and SOFTIGEN 767 were added to the water solution and mixed until well dispersed. The hair spray formulation was applied to hair tresses by means of a pump. No flaking was observed after drying and brushing the tresses. In addition, the hair spray formulation provided the hair with good hold properties without a tacky or sticky feel.

EXAMPLE VIII

Hair spray was prepared according to the following formulation:

| Ingredient | Weight % |
| --- | --- |
| Distilled Water | 56.97 |
| HYDROTRITICUM WAA | 0.20 |
| 28% Dispersion of Sulfo-Polyester B | 40.83 |
| Glycerol Diacetate | 2.00 |

This hair spray formulation was prepared by adding the HYDROTRITICUM WAA, the 28% dispersion of Sulfo-Polyester B, glycerol diacetate, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

EXAMPLE IX

Hair spray was prepared according to the following formulation:

| Ingredient | Weight % |
| --- | --- |
| Distilled Water | 56.97 |
| HYDROTRITICUM WAA | 0.20 |
| 28% Dispersion of Sulfo-Polyester B | 40.83 |
| Glycol Monoacetate | 2.00 |

This hair spray formulation was prepared by adding the HYDROTRITICUM WAA, the 28% dispersion of Sulfo-Polyester B, glycol monoacetate, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

EXAMPLE X

Hair spray was prepared according to the following formulation:

| Ingredient | Weight % |
| --- | --- |
| Distilled Water | 34.97 |
| HYDROTRITICUM WAA | 0.20 |
| 28% Dispersion of Sulfo-Polyester B | 40.83 |
| Propylene Glycol | 24.00 |

This hair spray formulation was prepared by adding the HYDROTRITICUM WAA, the 28% dispersion of Sulfo-Polyester B, propylene glycol, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

EXAMPLE XI

Hair spray was prepared according to the following formulation:

| Ingredient | Weight % |
| --- | --- |
| Distilled Water | 58.96 |
| HYDROTRITICUM WAA | 0.20 |
| 28% Dispersion of Sulfo-Polyester B | 40.83 |
| Dow Corning 190 Surfactant | 0.01 |

This hair spray formulation was prepared by adding the HYDROTRITICUM WAA, the 28% dispersion of Sulfo-Polyester B, Dow Corning 190 Surfactant, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

EXAMPLE XII

A hair spray was prepared according to Example XI except that the Dow Corning 190 Surfactant was increased to 0.05 weight percent. A 70/30 ratio of the hair spray to dimethyl ether was prepared. The all aqueous aerosol formulation showed good clarity and storage stability. The formulation was applied in the form of an aerosol hair spray to hair tresses. Flaking was observed while drying and brushing the tresses.

EXAMPLE XIII

Hair spray was prepared according to the following formulation:

| Ingredient | Weight % |
| --- | --- |
| Distilled Water | 58.67 |
| HYDROTRITICUM WAA | 0.20 |
| 28% Dispersion of Sulfo-Polyester B | 40.83 |
| FINSOLVE 355 | 0.30 |

This hair spray formulation was prepared by adding the HYDROTRITICUM WAA, the 28% dispersion of Sulfo-Polyester B, FINSOLVE 355, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

EXAMPLE XIV

Hair spray was prepared according to the following formulation:

| Ingredient | Weight % |
| --- | --- |
| Distilled Water | 58.67 |
| 28% dispersion of Sulfo-Polyester B | 40.83 |
| FINSOLVE 355 | 0.50 |

This hair spray formulation was prepared by adding the 28% dispersion of Sulfo Polyester B, FINSOLVE 355, water and mixing until well dispersed. The pH was determined to be 5.0 to 5.5. A 70/30 ratio of the hair spray to dimethyl ether was prepared. The formulation was applied in the form of an aerosol hair spray to hair tresses. Flaking was observed after drying and brushing the tresses.

Many variations will suggest themselves to those skilled in this art in light of the above detailed description. All such obvious modifications are within the full intended scope of the appended claims.

What is claimed is:

1. A hair spray formulation consisting essentially of:
   (1) a sulfo polyester having a Tg of 33° C. to 60° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol;
   (2) a polyethylene glycol ester of a mixture of caprylic and capric acids which is selected from the group consisting of

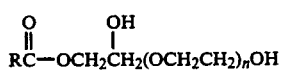

and mixtures thereof,
wherein R is $CH_3(CH_2)_n$ and n is 4 to 10;
   (3) an alpha hydroxy carboxylic acid having 2 to 6 carbon atoms; and
   (4) a liquid vehicle selected from the group consisting of water and a water/alcohol mixture.

2. A hair spray formulation consisting essentially of:
   (1) 1 to 10 weight percent based on the weight of components (1), (2), (3) and (4) of a sulfo polyester having a Tg of 33° C. to 60° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) 0.5 to 5.0 weight percent of a polyethylene glycol ester of a mixture of caprylic and capric acids which is selected from the group consisting of $$\overset{O}{\overset{\|}{R C}}-(OCH_2CH_2)_n OH$$

$$\overset{O}{\overset{\|}{R C}}-OCH_2CH_2\overset{OH}{\overset{|}{(OCH_2CH_2)}}_n OH$$

and mixtures thereof,
wherein R is $CH_3(CH_2)_n$ and n is 4 to 10;
   (3) 0.5 to 5.0 weight percent of an alpha-hydroxy carboxylic acid having 2 to 6 carbon atoms; and
   (4) 46 to 94 weight percent of a liquid vehicle selected from the group consisting of water and a alcohol mixture.

3. A hair spray formulation consisting essentially of:
   (1) 3 to 7 weight percent based on the weight of components (1), (2), (3) and (4) of a sulfo-polyester having a glass transition temperature of 33° C. to 60° C. consisting essentially of repeat units from
      (a) a dicarboxylic acid selected from the group consisting of aromatic dicarboxylic acids, saturated aliphatic dicarboxylic acids, cycloaliphatic dicarboxylic acids, and combinations thereof;
      (b) a diol; and
      (c) a difunctional sulfomonomer containing at least one sulfonate group attached to an aromatic nucleus wherein the functional groups are hydroxy, carboxy or amino, provided the difunctional sulfomonomer is present in an amount from 4 to 25 mole percent based on 100 mole percent dicarboxylic acid and 100 mole percent diol; and
   (2) 1 to 3 weight percent of a polyethylene glycol ester of a mixture of caprylic and capric acids which is selected from the group consisting of

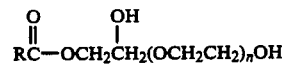

and mixtures thereof,
wherein R is $CH_3(CH_2)_n$ and n is 4 to 10;
   (3) 1 to 3 weight percent of an alpha-hydroxy carboxylic acid having 2 to 6 carbon atoms; and
   (4) 55 to 70 weight percent of a liquid vehicle selected from the group consisting of water and a water/alcohol mixture.

4. The hair spray formulation of claim 1 wherein the dicarboxylic acid component is selected from the group consisting of terephthalic acid, phthalic acid, isophthalic acid, naphthalene-2,6-dicarboxylic acid, cyclohexanedicarboxylic acid, cyclohexanediacetic acid, and mixtures thereof.

5. The hair spray formulation of claim 4 wherein the dicarboxylic acid component is isophthalic acid.

6. The hair spray formulation of claim 1 wherein the diol component is selected from the group consisting of ethylene glycol, diethylene glycol, triethylene glycol, 1,4-cyclohexanedimethanol, and mixtures thereof.

7. The hair spray formulation of claim 6 wherein the diol component is a mixture of diethylene glycol and 1,4-cyclohexanedimethanol.

8. The hair spray formulation of claim 1 wherein the difunctional sulfomonomer component is selected from the group consisting of sulfophthalic acid, sulfoterephthalic acid, sulfoisophthalic acid, 4-sulfonaphthalene-2,7-dicarboxylic acid, and esters thereof.

9. The hair spray formulation of claim 8 wherein the difunctional sulfomonomer component is 5-sodio-sulfoisophthalic acid.

10. The hair spray formulation of claim 1 wherein the sulfo-polyester, component (1), has repeat units from isophthalic acid, diethylene glycol and 1,4-cyclohexanedimethanol, and 5-sodio-sulfoisophthalic acid.

11. The hair spray formulation of claim 1 wherein the polyethylene glycol ester of a mixture of caprylic and capric acids, component (2), is

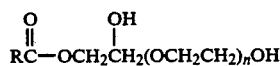

wherein RCO is a mixture of caprylic and capric radicals and n has an average value of 6.

12. The hair spray formulation of claim 1 wherein the polyethylene glycol ester of a mixture of caprylic and capric acids, component (2), is

wherein RCO is a mixture of caprylic and capric radicals and n has an average value of 8.

13. The hair spray formulation of claim 1 wherein the alpha-hydroxy carboxylic acid having 2 to 6 carbon atoms, component (3), is lactic acid.

14. The hair spray formulation of claim 1 wherein the alcohol component of the water/alcohol mixture, component (4), is selected from the group consisting of ethanol, isopropanol, t-butanol and mixtures thereof.

15. The hair spray formulation of claim 1 which additionally contains 3 to 40 weight percent based on the weight of components (1), (2), (3), and (4) of a propellant selected from the group consisting of a $C_1$-$C_4$ aliphatic hydrocarbon, dimethyl ether, and mixtures thereof.

16. The hair spray formulation of claim 15 wherein the dimethyl ether propellant is present in an amount of 30 to 40 weight percent based on the weight of components (1), (2), (3), and (4).

17. The hair spray formulation of claim 15 wherein the $C_1$-$C_4$ aliphatic hydrocarbon propellant is selected from the group consisting of methane, ethane, propane, n-butane, isobutane, and mixtures thereof.

18. The hair spray formulation of claim 17 wherein the propellant is a mixture containing about 83 weight percent isobutane and about 17 weight percent propane.

19. The hair spray formulation of claim 1 which additionally contains an additive selected from the group consisting of preservatives, fragrances, antifoaming agents, hair conditioners and plasticizers.

* * * * *

UNITED STATES PATENT AND TRADEMARK OFFICE
CERTIFICATE OF CORRECTION

PATENT NO. : 5,320,836
DATED : June 14, 1994
INVENTOR(S) : Andy H. Singleton

It is certified that error appears in the above-indentified patent and that said Letters Patent is hereby corrected as shown below:

The following formula in Column 2, lines 42-44 should be

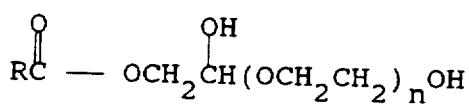

The following formula in Column 4, lines 2-4

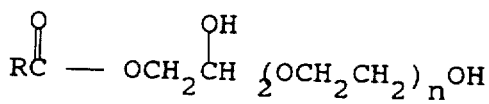

should be

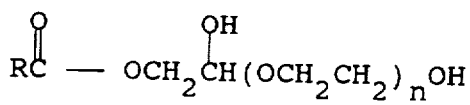

UNITED STATES PATENT AND TRADEMARK OFFICE
CERTIFICATE OF CORRECTION

PATENT NO. : 5,320,836
DATED : June 14, 1994
INVENTOR(S) : Andy H. Singleton

It is certified that error appears in the above-indentified patent and that said Letters Patent is hereby corrected as shown below:

The following formula in Column 4, lines 14-16 should be

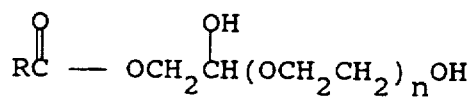

The following formula in Column 11, lines 5-7

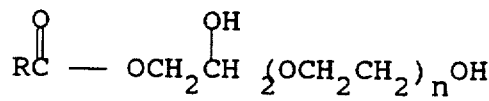

should be

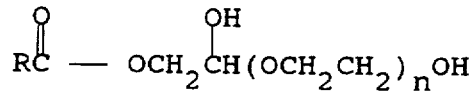

UNITED STATES PATENT AND TRADEMARK OFFICE
CERTIFICATE OF CORRECTION

PATENT NO. : 5,320,836
DATED : June 14, 1994
INVENTOR(S) : Andy H. Singleton

It is certified that error appears in the above-indentified patent and that said Letters Patent is hereby corrected as shown below:

The following formula in Column 11, lines 41-43 should be

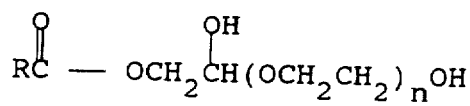

The following formula in Column 12, lines 8-10

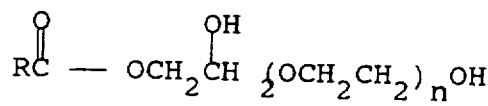

should be

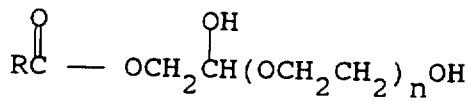

UNITED STATES PATENT AND TRADEMARK OFFICE
CERTIFICATE OF CORRECTION

PATENT NO. : 5,320,836
DATED : June 14, 1994
INVENTOR(S) : Andy H. Singleton

It is certified that error appears in the above-indentified patent and that said Letters Patent is hereby corrected as shown below:

The following formula in Column 12, lines 51-53 should be

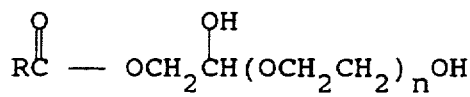

Signed and Sealed this

Twenty-fourth Day of October, 1995

BRUCE LEHMAN

Attest:

Attesting Officer

Commissioner of Patents and Trademarks